United States Patent
Park (10) Patent No.: US 11,817,199 B2
(45) Date of Patent: Nov. 14, 2023

(54) BRACHYTHERAPY APPLICATOR FORMATION METHOD AND APPARATUS

(71) Applicant: Varian Medical Systems, Inc., Palo Alto, CA (US)

(72) Inventor: Rebecca Park, Crawley (GB)

(73) Assignee: Varian Medical Systems, Inc., Palo Alto, CA (US)

( * ) Notice: Subject to any disclaimer, the term of this patent is extended or adjusted under 35 U.S.C. 154(b) by 730 days.

(21) Appl. No.: 16/713,594

(22) Filed: Dec. 13, 2019

(65) Prior Publication Data

US 2021/0183492 A1    Jun. 17, 2021

(51) Int. Cl.

| | |
|---|---|
| A61B 8/00 | (2006.01) |
| G16H 20/40 | (2018.01) |
| G16H 30/40 | (2018.01) |
| G06Q 50/04 | (2012.01) |
| G16H 40/63 | (2018.01) |
| G06F 30/20 | (2020.01) |
| A61N 5/10 | (2006.01) |
| G05B 19/4099 | (2006.01) |

(52) U.S. Cl.
CPC ........... *G16H 20/40* (2018.01); *A61N 5/1007* (2013.01); *G05B 19/4099* (2013.01); *G06F 30/20* (2020.01); *G06Q 50/04* (2013.01); *G16H 30/40* (2018.01); *G16H 40/63* (2018.01); *A61N 2005/1024* (2013.01); *G05B 2219/49023* (2013.01)

(58) Field of Classification Search
CPC ........ G16H 30/20; G16H 30/40; G16H 20/40; A61N 5/1007
See application file for complete search history.

(56) References Cited

U.S. PATENT DOCUMENTS

| | | | |
|---|---|---|---|
| 10,286,197 B2 | 5/2019 | Pouliot | |
| 2015/0265849 A1* | 9/2015 | Krechting | A61B 34/10 264/129 |

FOREIGN PATENT DOCUMENTS

CN     206762043 U     12/2017

OTHER PUBLICATIONS

Likhacheva, Anna O. et al. "Skin Surface Brachytherapy: A Survey of Contemporary Practice Patterns," Brachytherapy 16 (2017) pp. 223-229.

Jones, Emma-Louise et al. "Introduction of Novel 3D-Printed Superficial Applicators for High-Dose-Rate Skin Brachytherapy," Brachytherapy 16 (2017) pp. 409-414.

(Continued)

*Primary Examiner* — Joel F Brutus
(74) *Attorney, Agent, or Firm* — Fitch, Even, Tabin & Flannery LLP (57) ABSTRACT

A brachytherapy applicator is formed to use when administering therapeutic radiation to a particular patient's targeted area via brachytherapy. This process accesses image information for a patient that includes the targeted area and at least some adjacent non-targeted area. A control circuit uses that image information with prescribed dosing information for that patient to automatically generate a brachytherapy applicator design specifically to treat the particular patient's targeted area via brachytherapy. A corresponding brachytherapy applicator is then manufactured as a function, at least in part, of the brachytherapy applicator design to provide a manufactured brachytherapy applicator.

21 Claims, 4 Drawing Sheets

(56) References Cited

OTHER PUBLICATIONS

Adaptiiv Medical Technologies, Inc.; Brachytherapy Applicator product guide from https://www.adaptiiv.com/products/brachytherapy-applicator/; publicly available before Jul. 9, 2019.

* cited by examiner

BRACHYTHERAPY APPLICATOR FORMATION METHOD AND APPARATUS

TECHNICAL FIELD

These teachings relate generally to brachytherapy and more particularly to the formation and use of brachytherapy applicators.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume. A so-called treatment plan often serves in the foregoing regards.

Brachytherapy is a form of radiotherapy where one or more sealed radiation sources are physically placed inside or at least near to a patient's target treatment volume. The radiation source is often moved along one or more channels that comprise a part of a brachytherapy applicator to specific locations where the radiation source is allowed to momentarily dwell for a predetermined amount of time. Brachytherapy treatment plans often specify particular locations along particular channels where the radiation source is manually or automatically momentarily positioned for the predetermined dwell time.

While often a very effective therapy, brachytherapy applicators often represent a number of trade-offs. For example, one or more of the channels may not be ideally located (in whole or in part) to effectively achieve the desired irradiation of the patient's target volume while sparing as much as possible other volumes such as organs at risk.

In some cases a brachytherapy applicator is custom made to better suit the specifics of a given patient's situation. Unfortunately, this often requires a skilled person and generally represents a very time-consuming process that may not, in the end, represent a desired result. In addition, the applicant has determined that prior art approaches to radiation treatment plan optimization using a custom-made brachytherapy applicator only poorly leverage the available potential opportunities. For example, once an applicator is created, it can consume several hours to generate a corresponding radiation treatment plan since all the channels must be digitized and the dose distribution needs adapted around the applicator.

BRIEF DESCRIPTION OF THE DRAWINGS

The above needs are at least partially met through provision of the brachytherapy applicator formation method and apparatus described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments serve to facilitate forming a brachytherapy applicator to use when administering therapeutic radiation to a particular patient's targeted area. This includes accessing image information for the particular patient that includes the targeted area and at least some adjacent non-targeted area or areas. A control circuit uses that image information along with prescribed dosing information for the particular patient to automatically generate a brachytherapy applicator design specifically to treat the particular patient's targeted area via brachytherapy. A corresponding brachytherapy applicator is then manufactured as a function, at least in part, of the brachytherapy applicator design to provide a manufactured brachytherapy applicator.

These teachings are highly flexible in practice and practical as well. By one approach, for example, the aforementioned targeted area can include an area of skin for the particular patient. As another example, these teachings will accommodate using any of a variety of different kinds of imaging information including but not limited to three-dimensional images obtained using any of computed tomography, magnetic resonance, optically-scanned image information, or other methodologies known in the art.

By one approach, the automatic generation of the brachytherapy applicator design includes automatically setting at least one channel parameter. Examples in these regards include but are not limited to a distance that separates at least two channels (including but not limited to channel pitch), an angle between two channels, a degree of curvature for a channel, and an extent to which at least two channels are non-parallel to one another. In any or all of these cases the control circuit can be configured to select the particular parameter from only amongst a permitted range of available candidate values.

By one approach the aforementioned manufacturing of the brachytherapy applicator includes use of an additive manufacturing platform such as a three-dimensional printer.

By one approach the control circuit can access image information for the manufactured brachytherapy applicator and then use that image information to optimize a radiation treatment plan that includes optimized radioactive source locations (using the channels of the brachytherapy applicator) and dwell times to thereby provide an optimized radiation treatment plan. The latter can then be used to administer therapeutic radiation to the particular patient's targeted area.

So configured, a brachytherapy applicator custom designed for a particular patient can be readily and relatively quickly specified and manufactured. At least some of the specifics of the brachytherapy applicator can be selected to improve the likely efficacy of the plan when used to administer therapeutic radiation to the particular patient's targeted area.

Figure 1:
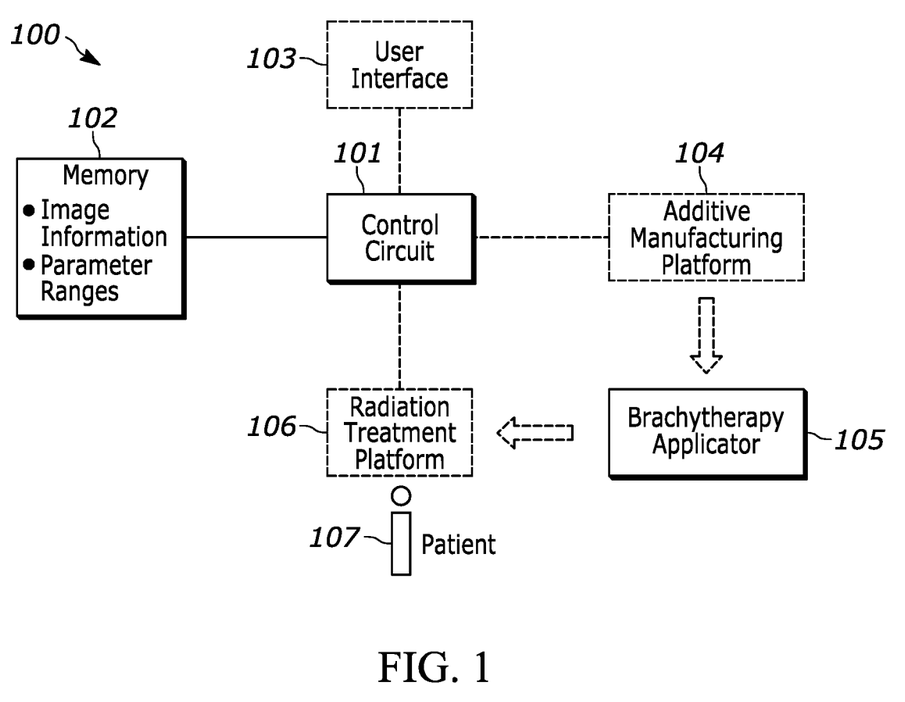
FIG. 1 comprises a block diagram as configured in accordance with various embodiments of these teachings.

These and other benefits may become clearer upon making a thorough review and study of the following detailed description. Referring now to the drawings, and in particular to FIG. 1, an illustrative apparatus 100 that is compatible with many of these teachings will be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

This illustrative example the control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to image information and parameter ranges as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By another optional approach the control circuit 201 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

By yet another optional approach (in lieu of the foregoing or in combination therewith) the control circuit 201 operably couples to an additive manufacturing platform 104 such as a so-called 3-D printer. By this operable coupling, and as desired, the control circuit 101 may provide printing files and/or otherwise control the operation of the additive manufacturing platform 104 or may simply provide the design information described herein for a brachytherapy applicator to the additive manufacturing platform 104.

So configured, the additive manufacturing platform 104 can manufacture a brachytherapy applicator 105 per the design of the control circuit 101 as described herein. (Additive manufacturing platforms in general, and 3-D printers in particular, comprise a well-understood area of prior art endeavor. Accordingly, further discussion in those regards is not presented here for the sake of brevity.)

By yet another optional approach (and again in lieu of the foregoing or in combination therewith, the control circuit 201 operably couples to a radiation treatment platform 106. The radiation treatment platform 106 is configured to deliver therapeutic radiation to a corresponding patient 107 by way of brachytherapy. In application settings where one or more of the radioactive sources are to be automatically placed/moved, the radiation treatment platform 106 can include a so-called afterloader that functions to move a radioactive source along a corresponding channel to a particular location for a particular dwell time. Depending upon the specifics of the radiation treatment plan, a given radiation source may dwell at a number of locations along any given channel.

Figure 2:
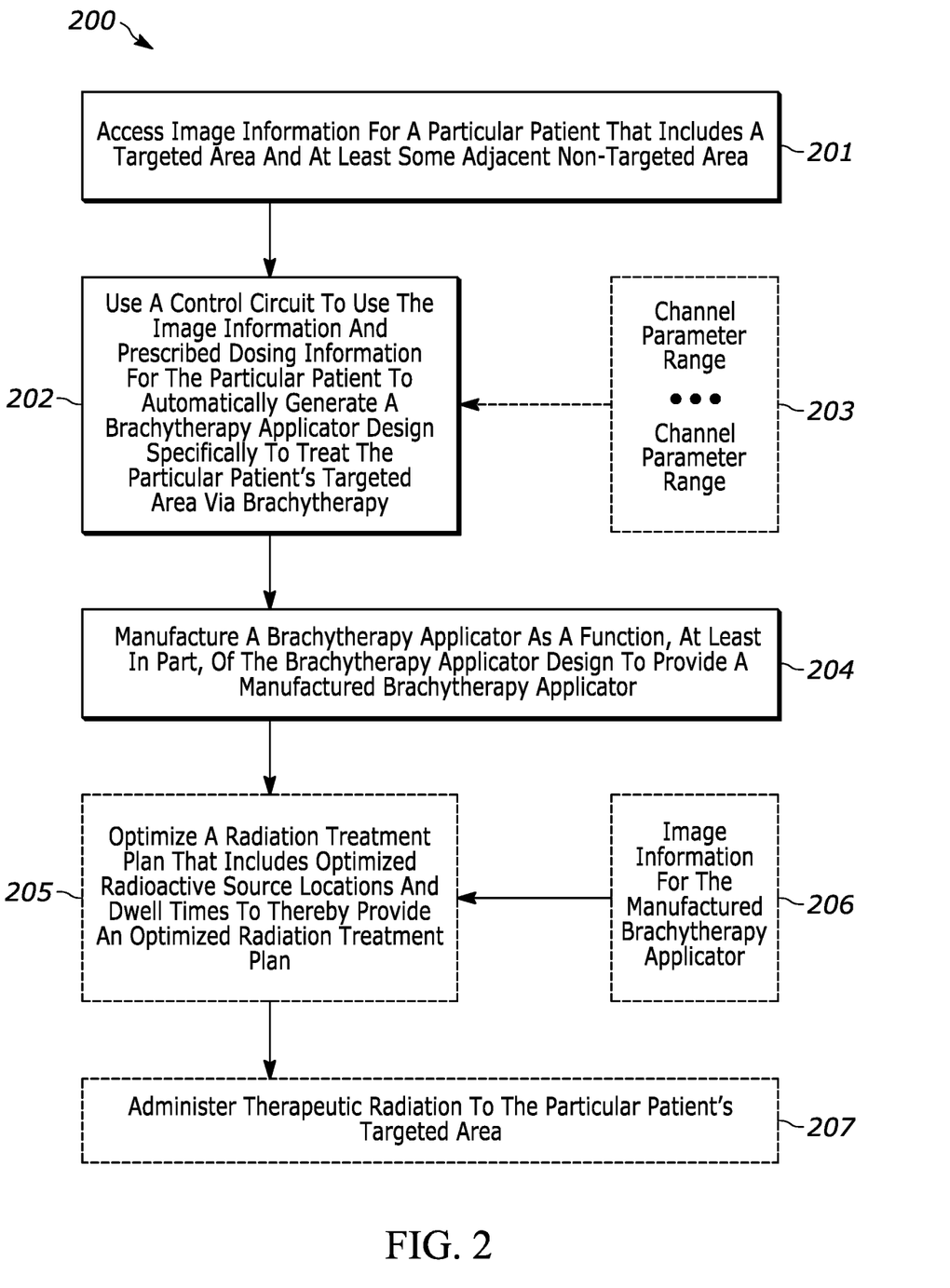
FIG. 2 comprises a flow diagram as configured in accordance with various embodiments of these teachings.

With continued reference to FIG. 1, and referring now as well to FIG. 2, a process 200 to manufacture a brachytherapy applicator 105 will be described.

At block 201, the control circuit 101 accesses image information for a particular patient 107. By one approach the control circuit 101 accesses the above-described memory 102 to obtain some or all of this image information. The image information includes the targeted area to receive radiation (such as a tumor) and at least some adjacent non-targeted area (such as any of a variety of tissues, organs, and so forth that are closely to the side of, in front of, or behind the targeted area).

These teachings will accommodate a variety of different types of image information. By one approach the image information comprises three-dimensional images. Examples include but are not limited to computed tomography (CT) images, magnetic resonance (MR) information, and optically-scanned image information. The utilized information may all be of a same kind of information (such as all comprising CT images) or may be a mix of different kinds of image information as desired.

At block 202, this process 200 provides for using the control circuit 101 to use the accessed image information along with prescribed dosing information for the particular patient 107 to automatically generate a brachytherapy applicator design specifically to treat the particular patient's targeted area via brachytherapy. The prescribed dosing information may specify, for example, a desired minimum level of radiation dosing (expressed, for example, using Gray units) for the targeted area along with a desired maximum level of radiation dosing for at least some part of the aforementioned non-targeted area.

In this illustrative example the brachytherapy applicator design will presume use of the aforementioned additive manufacturing platform 104, and in particular will presume the use of a 3-D printer. In a typical application setting the brachytherapy applicator 105 will be formed using an appropriate plastic material (and possibly a radio-transparent plastic material). These teachings will also accommodate, however, using essentially any other material of choice. With momentary reference to FIG. 3, the design of the brachytherapy applicator 105 may intentionally conform to some corresponding patient surface. For example, when the resultant brachytherapy applicator 105 is designed to be disposed adjacent to a particular external surface of the patient 107, the brachytherapy applicator 105 can have a main body 301 that is shaped to conform to that body portion.

Figure 3:
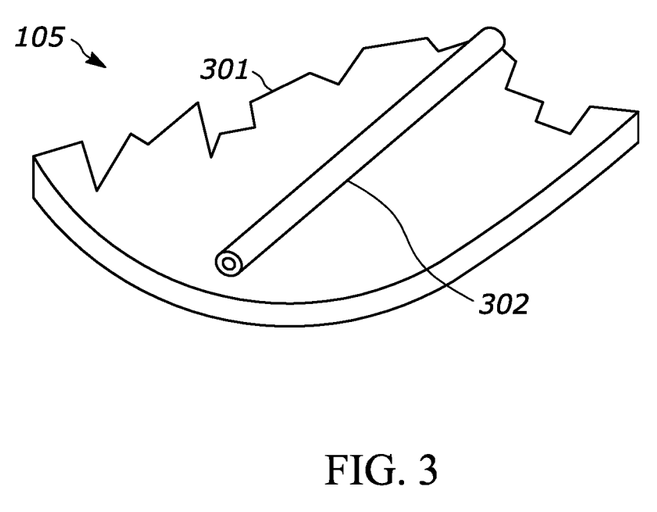
FIG. 3 comprises a perspective view as configured in accordance with various embodiments of these teachings.

In the alternative, the body 301 of the brachytherapy applicator 105 can be comprised of a slightly flexible material. So configured, the brachytherapy applicator 105 can be manipulated as necessary when fitted to the patient to conform to the relevant part of the patient's body. (In a typical application setting the brachytherapy applicator 105 will be held in its deployed position on the patient's body using an appropriate adhesive and/or adhesive tape or the like).

The design of the brachytherapy applicator 105 will also be sized to ensure appropriate coverage of the targeted area. The size and or shape of the brachytherapy applicator 105 may also be selected to help ensure that the brachytherapy applicator 105 can be appropriately and securely affixed to the patient 107.

The design of the brachytherapy applicator 105 will also include one or more channels 302 to receive a brachytherapy radiation source. Accordingly, the channel will have a typically cylindrical form factor to readily receive such a source or applicator channel such as a closed ended catheter. Presuming use of a 3-D printer, these channels 302 will be comprised of a same material as the main body 301 and will typically be formed integral to the latter as well.

Figure 4:
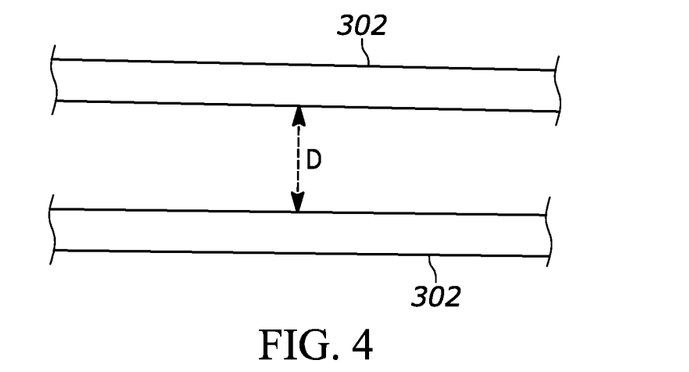
FIG. 4 comprises a top plan view as configured in accordance with various embodiments of these teachings.
Figure 5:
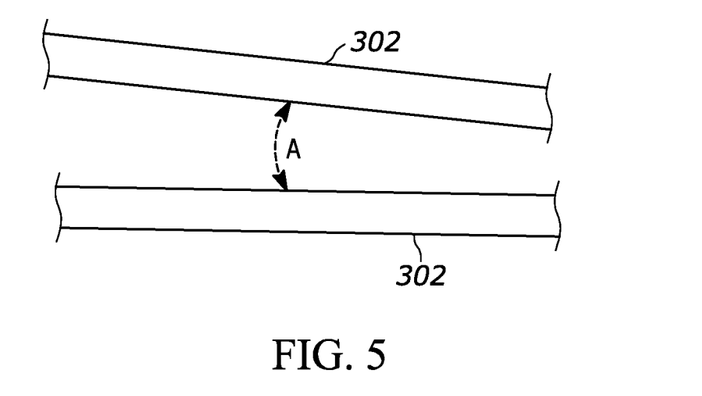
FIG. 5 comprises a top plan view as configured in accordance with various embodiments of these teachings.
Figure 6:
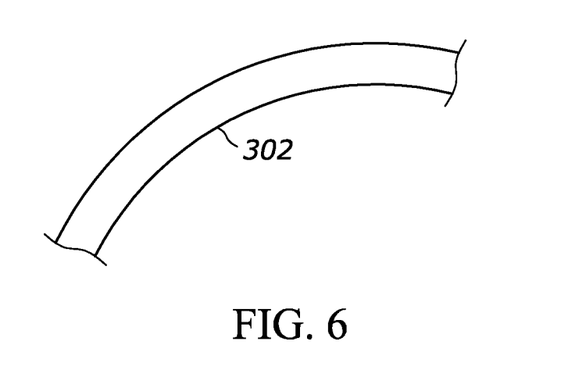
FIG. 6 comprises a top plan view as configured in accordance with various embodiments of these teachings.

Pursuant to these teachings, the aforementioned design of the brachytherapy applicator 105 can provide for a customized selection of a number of channels. In addition, the design can provide for a customized set of parameters regarding those channels. With momentary reference to FIG. 4, by one approach such a parameter can specify the distance D between two such channels 302. If desired, the channels 302 can all be equally spaced from one another and hence the selectable parameter can comprise channel pitch. By another approach, in lieu of the foregoing or in combination therewith, and referring momentarily to FIG. 5, such a channel parameter can comprise an angle A between two such channels 302. By yet another approach, again in lieu of the foregoing or in combination therewith, and referring momentarily to FIG. 6, such a channel parameter can comprise a degree of curvature of a channel 302.

By one approach, the control circuit 101 is configured to automatically generate the brachytherapy applicator design by automatically setting one or more channel parameters after optimizing the brachytherapy applicator design with respect to at least one objective that corresponds to the prescribed dosing information. The latter activity can include automatically trying, in an incremental manner, a series of different values for each selected channel parameter. (Those skilled in the art will understand that optimization objectives provide a measure by which a process can test or assure that a particular specified dose is being uniformly administered through the patient's targeted area while avoiding undue dosing of other patient areas.)

If desired, such channel parameters may be selectable at any particular resolution or granularity and without limits. More typically, it may be beneficial to constrain each such parameter to a range of available candidate parameter values 203 from which the control circuit can select. These ranges can be based upon the physical limitations that characterize a specific radiation treatment platform. For example, when selecting a particular distance that separates two adjacent channels 302, the control circuit 101 may be unable to select a distance that exceeds a particular range of values and/or that is less than such a range. As another example, when selecting a particular angle between two adjacent channels 302, the control circuit 101 may be unable to select an angle that exceeds a particular range of values and/or that is less than such a range. And as yet another example, when selecting a particular degree of curvature for a given channel 302, the control circuit 101 may be unable to select a degree of curvature that exceeds a particular range of values and/or that is less than such a range.

If desired, the design of the brachytherapy applicator 105 can be informed by other parameters that are either automatically selected and/or user selected (or modified). Examples include target region information, treatment depth, applicator thickness, entry angle, and so forth.

Also if desired, these teachings will accommodate providing the user with an opportunity (for example, via the aforementioned user interface 103) to modify the automatically generated brachytherapy applicator design (for example, by modifying channels or other structures).

So configured, the control circuit 101 can design a brachytherapy applicator 105 that is well-suited, in terms of its size and shape, to be disposed upon a particular part of the patient's body (or potentially disposed within the patient's body) and which has channels suitably and particularly located to help ensure beneficial placement of radiation sources when administering radiation therapy to the particular patient 107.

At block 204, this process 200 provides for manufacturing a brachytherapy applicator (using, for example, the above-mentioned additive manufacturing platform 104) as a function, at least in part, of the brachytherapy applicator design to thereby provide a resultant manufactured brachytherapy applicator 105. By one approach, the control circuit 101 facilitates this activity by generating printing files based upon the brachytherapy applicator design.

Although the radiation treatment plan has already been optimized, by one optional approach and with the specifics of the brachytherapy applicator's physical layout and dimensions now being precisely known and as shown at optional block 205, this process 200 can provide for again optimizing the radiation treatment plan for the particular patient 107 that makes use of accessed image information 206 for the manufactured brachytherapy applicator 105. In particular, using that image-based information regarding the precise locations of the channels and the intended disposition of the applicator 105 on (or in) the patient, the control circuit 101 can optimize a radiation treatment plan that includes optimized radioactive source locations and dwell times to thereby provide an optimized radiation treatment plan.

It will be understood that the expression "optimizing" should not be confused with the idea of identifying an objectively "optimum" plan that is superior to all other possible plans. Instead, such optimization comprises iteratively assessing alternatives (such as the use of alternative physical parameters for various aspects of the proposed treatment) to a given plan to typically identify a series of successively-better plans. As used herein, "optimization" will be understood to refer to improving a candidate treatment plan without necessarily ensuring that the optimized result is, in fact, the singular best solution.

At optional block 207, if desired the manufactured brachytherapy applicator 105 and the optimized radiation treatment plan can be used to administer therapeutic radiation via brachytherapy to the particular patient's targeted area. The use of a treatment plan and a brachytherapy applicator to administer therapeutic radiation constitutes a well understood area of prior art endeavor that requires no further elaboration here.

These teachings facilitate manufacturing and using a brachytherapy applicator via an approach that does not require a highly skilled technician and hence constitutes a significant improvement over prior art approaches in those regards.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method to facilitate forming a brachytherapy applicator to use when administering therapeutic radiation to a particular patient's targeted area, the method comprising:
   accessing image information for the particular patient that includes the targeted area and at least some adjacent non-targeted area;
   using a control circuit to use the image information and prescribed dosing information for the particular patient to automatically generate a brachytherapy applicator design specifically to be disposed externally upon a particular part of the particular patient's body to treat the particular patient's targeted area via brachytherapy;
   manufacturing a brachytherapy applicator as a function, at least in part, of the brachytherapy applicator design to provide a manufactured brachytherapy applicator.

2. The method of claim 1 wherein the targeted area includes an area of skin for the particular patient.

3. The method of claim 1 wherein the image information comprises at least one of the following three-dimensional images:
   computed tomography (CT) information;
   magnetic resonance (MR) information;
   optically-scanned image information.

4. The method of claim 1 wherein the control circuit is configured to automatically generate the brachytherapy applicator design by automatically setting at least one channel parameter.

5. The method of claim 4 wherein the at least one channel parameter comprises at least one of:
   channel pitch;
   angle.

6. The method of claim 4 wherein the at least one channel parameter comprises a distance that separates at least two channels.

7. The method of claim 6 wherein the control circuit is configured to select the distance from amongst a range of available candidate distances.

8. The method of claim 4 wherein the at least one channel parameter comprises a degree of curvature of at least one channel.

9. The method of claim 8 wherein the control circuit is configured to select the degree of curvature from amongst a range of available candidate degrees of curvature.

10. The method of claim 4 wherein the at least one channel parameter comprises an extent to which at least two channels are non-parallel to one another.

11. The method of claim 4 wherein the control circuit is configured to automatically generate the brachytherapy applicator design by automatically setting the at least one channel parameter after optimizing the brachytherapy applicator design with respect to at least one objective that corresponds to the prescribed dosing information.

12. The method of claim 1 further comprising:
   manufacturing a brachytherapy applicator as a function, at least in part, of the brachytherapy applicator design to provide a manufactured brachytherapy applicator.

13. The method of claim 12 wherein manufacturing the brachytherapy applicator comprising using additive manufacturing to manufacture the brachytherapy applicator design to thereby provide the manufactured brachytherapy applicator.

14. The method of claim 13 wherein the additive manufacturing comprises three-dimensional printing.

15. The method of claim 12 further comprising:
   using a control circuit to access image information for the manufactured brachytherapy applicator and then to use the image information for the manufactured brachytherapy applicator to optimize a radiation treatment plan that includes optimized radioactive source locations and dwell times to thereby provide an optimized radiation treatment plan.

16. The method of claim 15 further comprising:
   using the manufactured brachytherapy applicator and the optimized radiation treatment plan to administer therapeutic radiation to the particular patient's targeted area.

17. An apparatus to facilitate forming a brachytherapy applicator to use when administering therapeutic radiation to a particular patient's targeted area, the apparatus comprising:
   a control circuit configured to:
      access image information for the particular patient that includes the targeted area and at least some adjacent non-targeted area,
      use the image information and prescribed dosing information for the particular patient to automatically generate a brachytherapy applicator design specifically to be disposed externally upon a particular part of the particular patient's body to treat the particular patient's targeted area via brachytherapy;
   an additive manufacturing platform configured to manufacture a brachytherapy applicator as a function, at least in part, of the brachytherapy applicator design to provide a manufactured brachytherapy applicator.

18. The apparatus of claim 17 wherein the control circuit is configured to automatically generate the brachytherapy applicator design by automatically setting at least one channel parameter.

19. The apparatus of claim 18 wherein the at least one channel parameter comprises at least one of:
   channel pitch;
   angle.

20. The apparatus of claim 18 wherein the at least one channel parameter comprises a distance that separates at least two channels.

21. The apparatus of claim 20 wherein the control circuit is configured to select the distance from amongst a range of available candidate distances.

\* \* \* \* \*